(12) United States Patent
Biel

(10) Patent No.: US 8,267,982 B2
(45) Date of Patent: Sep. 18, 2012

(54) PHOTODYNAMIC CELLULAR AND ACELLULAR ORGANISM ERADICATION UTILIZING A PHOTOSENSITIVE MATERIAL AND SURFACTANT

(75) Inventor: Merrill A. Biel, Mendota Heights, MN (US)

(73) Assignee: Advanced Photodynamic Technologies, Inc., Minneapolis, MN (US)

( * ) Notice: Subject to any disclaimer, the term of this patent is extended or adjusted under 35 U.S.C. 154(b) by 2134 days.

(21) Appl. No.: 09/792,578

(22) Filed: Feb. 23, 2001

(65) Prior Publication Data

US 2002/0183808 A1    Dec. 5, 2002

(51) Int. Cl.
*A61N 5/06*    (2006.01)

(52) U.S. Cl. .............................. 607/88; 606/7

(58) Field of Classification Search ............... 606/3, 4, 606/6–17; 607/88–96
See application file for complete search history.

(56) References Cited

U.S. PATENT DOCUMENTS

| | | | |
|---|---|---|---|
| 4,020,183 A | 4/1977 | Asculai et al. | |
| 4,181,128 A * | 1/1980 | Swartz | 607/88 |
| 4,656,186 A | 4/1987 | Bommer et al. | |
| 4,882,234 A * | 11/1989 | Lai et al. | 514/185 |
| 4,950,665 A | 8/1990 | Floyd | |
| 4,973,711 A | 11/1990 | Maienfisch | |
| 5,041,078 A | 8/1991 | Matthews et al. | |
| 5,062,431 A | 11/1991 | Potter | |
| 5,260,020 A * | 11/1993 | Wilk et al. | 606/15 |
| 5,262,401 A | 11/1993 | Vogel et al. | |
| 5,611,793 A | 3/1997 | Wilson et al. | |
| 5,616,342 A | 4/1997 | Lyons | |
| 5,676,959 A | 10/1997 | Heitz et al. | |
| 5,827,644 A | 10/1998 | Floyd et al. | |
| 5,882,328 A | 3/1999 | Levy et al. | |
| 6,251,127 B1 * | 6/2001 | Biel | 606/11 |
| 6,284,289 B1 * | 9/2001 | Van den Berghe | 424/746 |

OTHER PUBLICATIONS

Vaara et al. "Polycations Sensitize Enteric Bacteria to Antibiotics" Antimicrobial Agents & Chemotherapy: Jul. 1983; pp. 107-113, 1983.*
"Effects of Surface-active Agents on Drug Susceptibility Levels and Ultrastructure of *Mycobacterium avium* Complex Organisms Isolated from AIDS Patients"; Sandesh P. Naik, William A. Samsonoff, and Robert E. Ruck; Diagn Microbiol Infect Dis, 1989, 11:11-19.
"Differential Permeability for Lipaphilic Compounds in Uncoupler-Resistance Cells of *Escherichia coli*"; Edward G. Sedgwick and Philip D. Bragg; Biochimica et Biophysica ACTA, 1099 (1992) 45-50.
"Two Types of Haemolytic Activity of Detergents"; Jozef Bielawski; Biochimica•et Biophysica ACTA, 1035 (1990) 214-217.

(Continued)

*Primary Examiner* — David Shay
(74) *Attorney, Agent, or Firm* — Dobrusin & Thennisch PC

(57) ABSTRACT

The invention relates to a method of photoeradication of cellular and acellular organisms including the steps of providing a surface acting agent in association with a cellular or acellular organism, the surface acting agent disorienting a membrane structure so that said membrane no longer functions as an effective osmotic barrier; providing a photosensitive material in association with the cellular or acellular organism; and applying light in association with the cellular or acellular organism to cause a disruption of the organism. The method according to the present invention may be utilized in invitro and invivo treatment protocols for infections, sterilization procedures, cancer cell eradication, virus and fungus eradication, spore eradication, and biofilm organism eradication. Additional aspects of the invention include particular combinations of photosensitive materials and surfactants for use in photodynamic therapies.

73 Claims, 6 Drawing Sheets

Photoeradication using Methylene Blue mediated PDT & the Surfactant SDS

| Qualitative Colony Count | | | | | | | | |
|---|---|---|---|---|---|---|---|---|
| Score | Col. | | wave length = 664 nm | | | | | |
| 4 = | 301+. | | n/a = not applicable | | | | | |
| 3 = | 101-300. | | | | | | | |
| 2 = | 6-100. | | | | | | | |
| 1 = | 1-5. | | | | | | | |
| 0 = | 0 | | | | | | | |

| Organism ($9\times10^4$/mL) | Meth. Blue (µg/mL) | SDS % | Total Power (W) | Light Dose Rate (mW/cm²) | Light Dose (J/cm²) | No Light | Single Light Dose | Double Light Dose |
|---|---|---|---|---|---|---|---|---|
| Candida albicans | 100 | 0.0075 | 0.3 | 100 | 60 | 4 | 0 | 0 |
| | 100 | 0.01 | 0.3 | 100 | 60 | 4 | 1 | 0 |
| Escherichia coli | 25 | 0.003 | 0.127 | 100 | 40 | 4 | 0 | n/a |
| Pseudomonas aeruginosa | 100 | 0.003 | 0.23 | 150 | 60 | 4 | 4 | 1 |
| Staphylococcus aureus | 30 | 0.003 | 0.127 | 100 | 40 | 4 | 0 | n/a |
| | 30 | 0.005 | 0.127 | 100 | 40 | 4 | 0 | n/a |
| | 40 | 0.003 | 0.127 | 100 | 40 | 4 | 0 | n/a |
| | 40 | 0.005 | 0.127 | 100 | 40 | 4 | 0 | n/a |
| Streptococcus pneumoniae | 3 | 0.003 | 0.225 | 75 | 15 | 4 | 0 | n/a |
| | 3 | 0.005 | 0.225 | 75 | 15 | 4 | 0 | n/a |
| | 5 | 0.003 | 0.225 | 75 | 15 | 4 | 0 | n/a |
| | 5 | 0.005 | 0.225 | 75 | 15 | 4 | 0 | n/a |
| | 5 | 0.0075 | 0.225 | 75 | 15 | 4 | 0 | n/a |

OTHER PUBLICATIONS

"Rapid Bacterial Permeabilization Reagent Useful for Enzyme Assays"; Bio Techniques; The Journal of Laboratory Technology for Bioresearch; vol. 19, No. 1 Jul. 1995.

"Review Permeabilized Cells"; Hansruedi Felix; Analytical Biochemistry 120, 211-234 (1982).

"Disruptive Effects of TRIS and Sodium Lauroyo Sarcosinate the Outer Membrane of *Pseudomonas cepacia* Shown by Fluorescent Probes"; Hosmin Anwar, Michael R.W. Brown, Adam Z. Britten, and Peter A. Lambert; The Journal of General Microbiology; vol. 129, Part 7, Jul. 1983.

"Changes in the Permeability of the Blood-Brain Barrier Following Sodium Dodecyl Sulphate Administration in the Rat"; Antonella Saija, Pietro Princi, Domenico Trombetta, Maria Lanza, Anna De Pasquale; Experimental Brain Research (1997) 115:546-551.

"Effect of Surfactants on the Antibacterial Activity of Preservatives"; T.R.R. Kurup, Lucy S.C. Wan, L.W. Chan, Department of Pharmacy, National University of Singapore, Lower Kent Ridge Road, Singapore.

"Epithelial Transport of Drugs in Cell Culture. VII: Effects of Pharmaceutical Surfactant Excipients and Bile Acids on Transepitagelial Permeability in Monolayers of Human Intestinal Epithelial (CACO-2) Cells"; Eva Karin Anderberg, Christer Nystrom and Per Artursson; received Jul. 8, 1991 from the Department of Pharmaceuticals, Biomedical Centre, Uppsala University; Journal of Pharmaceutical Sciences; vol. 81, No. 9, Sep. 1992; pp. 879-887.

"Epithelial Transport of Drugs in Cell Culture. VIII: Effects of Sodium Dodecyl Sulphate on Cell Membrane and Tight Junction Permeability in Human Intestinal Epithelial (CACO-2) Cells"; Eva Karin Anderberg and Per Artursson; received Mar. 17, 1992, from the Department of Pharmaceuticals, Biomedical Center, Uppsala University; Journal of Pharmaceutical Sciences; vol. 82, No. 4, Apr. 1993; pp. 392-398.

"Do Salicylates and Ascorbate Increase the Outer Membrane Permeability to Hydrophobic Antibiotics in *Pseudomonas aeruginosa*"; Vaara M.; Drugs Under Experimental and Clinical Research; pp. 569-574, 1990.

"Agents That Increase the Permeability of the Outer Membrane"; Martti Vaara; Department of Bacteriology and Immunology, University of Helsinki, 00290 Helsinki, Finland; Microbiological Reviews, Sep. 1992, pp. 395-411.

"Fate and Effects of the Surfactant Sodium Dodecyl Sulfate"; Michael M. Singer and Ronald S. Tjeerdema; Reviews of Environmental Contamination and Toxicology, vol. 133; pp. 96-149, 1993.

"Inactivation of Gram-Negative Bacteria by Photosensitized Porphyrins"; Yeshayahu Nitzan, Mina Gutterman, Zvi Malik, and Benjamin Ehrenberg; Health Sciences Research Center, Department of Life Sciences and Department of Physics, Bar-Ilan University, Ramat-gan 52900, Israel; Photochemistry and Photobiology vol. 55, No. 1, pp. 89-96, 1992.

"pH Dependence of Sensitized Photooxidation in Micellar Anionic and Cationic Surfactants, using Thiazines Dye"; O. Bagno, H.C. Saulignac, and J.Joussot-Dubien; Photoche. Photobiol. 1979, 29(6):1079-1081.

Tarasov, Sergey G., et al., "Bisimidazoacridones: Effect of Molecular Environment on Conformation and Photophysical Properties," Photochemistry and Photobiology, 1999, 70(4): 568-578.

Danner, et al., "Purification, Toxicity, and Antiendotoxin Activity of Polymyxin B Nonapeptide" Antimicrobial Agents and Chemotherapy, Sep. 1989, pp. 1428-1434.

Reddi, et al., "Hash Photolysis Studies of Hemato- and Copro-Porphyrins in Homogeneous and Microhetemgeneous Aqueous Dispersions," Photochemistry and Photobiology, vol. 38, No. 6., pp. 639-645, 1983.

Mukerjee, et al., "Critical Micelle Concentrations of Aqueous Surfactant Systems,"NSRDS—NBS 36, Feb. 1971, pp. 51-53, 107-108, 140-141, and 154.

\* cited by examiner

Photoeradication using Methylene Blue mediated PDT & the Surfactant SDS

| | Qualitative Colony Count | | | | | | | | Single | Double |
|---|---|---|---|---|---|---|---|---|---|---|
| | Score | Col. | | wave length = 664 nm | | | | | Light | Light |
| | 4 = | 301+. | | n/a = not applicable | | | | | Dose | Dose |
| | 3 = | 101-300. | | | | | | | | |
| | 2 = | 6-100. | | | | | | | | |
| | 1 = | 1-5. | | | | | | | | |
| | 0 = | 0 | | | | | | | | |
| | Meth. Blue | | Total | Light Dose | Light Dose | No | | | | |
| Organism ($9 \times 10^8$/mL) | (µg/mL) | SDS % | Power (W) | Rate (mW/cm$^2$) | (J/cm$^2$) | Light | | | | |
| Candida albicans | 100 | 0.0075 | 0.3 | 100 | 60 | 4 | | | 0 | 0 |
| | 100 | 0.01 | 0.3 | 100 | 60 | 4 | | | 1 | 0 |
| Escherichia coli | 25 | 0.003 | 0.127 | 100 | 40 | 4 | | | 0 | n/a |
| Pseudomonas aeruginosa | 100 | 0.003 | 0.23 | 150 | 60 | 4 | | | 4 | 1 |
| Staphylococcus aureus | 30 | 0.003 | 0.127 | 100 | 40 | 4 | | | 0 | n/a |
| | 30 | 0.005 | 0.127 | 100 | 40 | 4 | | | 0 | n/a |
| | 40 | 0.003 | 0.127 | 100 | 40 | 4 | | | 0 | n/a |
| | 40 | 0.005 | 0.127 | 100 | 40 | 4 | | | 0 | n/a |
| Streptococcus pneumoniae | 3 | 0.003 | 0.225 | 75 | 15 | 4 | | | 0 | n/a |
| | 3 | 0.005 | 0.225 | 75 | 15 | 4 | | | 0 | n/a |
| | 5 | 0.003 | 0.225 | 75 | 15 | 4 | | | 0 | n/a |
| | 5 | 0.005 | 0.225 | 75 | 15 | 4 | | | 0 | n/a |
| | 5 | 0.0075 | 0.225 | 75 | 15 | 4 | | | 0 | n/a |

*FIG. 2*

| Oral Candidiasis MB/SDS Treatment Cultures | | | |
|---|---|---|---|
| λ: | 664 nm | | |
| Power: | | | |
| Light dose: | 275 J/cm | | |
| Lt. Ds. Rate: | 400 mW/cm | | |
| Time: | 687.5 sec | | |
| Qualitative Colony Count | Score | Colony count | |
| | 4= | 301+ | |
| | 3= | 101-300 | |
| | 2= | 6-100 | |
| | 1= | 1-5 | |
| Cultures | | | |
| 1 | [MB] | 50 ug/ml | meth. blue conc. |
| | [SDS] | 0.0075% | SDS conc. |
| | M-L- | 2(18) | colony count |
| | M+L- | 2(29) | colony count |
| | M+L+ | 0 | colony count |
| 2 | [MB] | 100 ug/ml | |
| | [SDS] | 0.0075% | |
| | M-L- | 2(55) | |
| | M+L- | 2(15) | |
| | M+L+ | 0 | |
| 3 | [MB] | 100 ug/ml | |
| | [SDS] | 0.0075% | |
| | M-L- | 2(9) | |
| | M+L- | 2(11) | |
| | M+L+ | 0 | |
| 4 | [MB] | 100 ug/ml | |
| | [SDS] | 0.0075% | |
| | M-L- | 2(6) | |
| | M+L- | 2(6) | |
| | M+L+ | 0 | |
| 5 | [MB] | 200 ug/ml | |
| | [SDS] | 0.0075% | |
| | M-L- | 1(2) | |
| | M+L- | 0 | |
| | M+L+ | 0 | |
| 6 | [MB] | 200 ug/ml | |
| | [SDS] | 0.0075% | |
| | M-L- | 2(7) | |
| | M+L- | 2(9) | |
| | M+L+ | 0 | |
| 7 | [MB] | 200 ug/ml | |
| | [SDS] | 0.0075% | |
| | M-L- | 2(7) | |
| | M+L- | 1(3) | |
| | M+L+ | 1(5) | |
| 8 | [MB] | 300 ug/ml | |
| | [SDS] | 0.0075% | |
| | M-L- | 2(9) | |
| | M+L- | 2(30) | |
| | M+L+ | 0 | |
| 9 | [MB] | 300 ug/ml | |
| | [SDS] | 0.0075% | |
| | M-L- | 0 | |
| | M+L- | 2(30) | |
| | M+L+ | 0 | |
| 10 | [MB] | 300 ug/ml | |
| | [SDS] | 0.0% | |
| | M-L- | 0 | |
| | M+L- | 2(12) | |
| | M+L+ | 1(1) | |

| Trial | Period | Organisms | MB | SDS | L- | L+ | L++ |
|---|---|---|---|---|---|---|---|
| 1 | 7 days | Enterococcus<br>Gram+bacillus, res. Corynebacterium<br>Gram+cocc<br>Staphylococcus aureus<br>Candida albicans | 100 µg/ml | .003% | 4 | 0 | n/a |
| 2 | 8 hours | Gram+ cocc<br>α Strep not Enterococcus<br>Staphylococcus, coag.-<br>α Strep not Enterococcus<br>Gram+ bacillus | 100 µg/ml | .003% | 4 | 0 | n/a |
| 3 | 2 days | α Strep not Enterococcus<br>α Strep not Enterococcus 2nd strain<br>Candida albicans<br>γ Strep not Enterococcus | 100 µg/ml | .003% | 4 | 2 | n/a |
| 4 | 5 days | α Strep not Enterococcus<br>Staphylococcus, coag.-<br>Staphylococcus, coag.- 2nd strain | 200 µg/ml | .003% | 3 | 2 | n/a |
| 5 | 1 day | Gram+bacillus, res. Corynebacterium<br>α Strept not Enterococcus<br>Candida albicans<br>Yeast not Candida or Cryptococcus | 200 µg/ml | .003% | 4 | 2 | n/a |
| 6 | 1 day | Klebsiella oxytoca<br>α Strep not Enterococcus<br>Staphylococcus, coag.-<br>γ Strep not Enterococcus<br>α Strep not Enterococcus<br>Haemophilus, not H influ. B lact.- | 200 µg/ml | .0075% | 4 | 2 | n/a |
| 7 | 1 day | Streptococcus pneumoniae<br>Stomatococcus probable<br>α Strep not Enterococcus<br>Staphylococcus, coag.- | 200 µg/ml | .0075% | 4 | 2 | 2(10) |
| 8 | 8 days | α Strept<br>α Strept 2nd strain<br>Staphylococcus, coag.-<br>Gram+ bacillus<br>Gram+ bacillus 2nd strain<br>Yeast | 200 µg/ml | .0075% | 4 | 2(41) | 0 |
| 9 | 2 weeks | Pseudomonas aeruginosa<br>Pseudomonas aeruginosa 2nd strain<br>Staphylococcus, coag.- | 200 µg/ml | .0075% | 4 | 2 | 2 |
| 10 | 12 days | Staphylococcus aureus<br>Gram+ bacillus, res. Corynebacterium<br>Proteus mirabilis | 250 µg/ml | .0075% | 4 | 4 | 4 |
| 11 | 1 day | α Strept<br>Staphylococcus, coag.-<br>α Strept 2nd strain<br>Gram+ bacillus<br>Gram+ bacillus, res. Corynebacterium | 200 µg/ml | .0075% | 4 | 1(5) | 2(8) |

FIGURE 4B

| Trial | Period | Organisms | MB | SDS | L- | L+ | L++ |
|---|---|---|---|---|---|---|---|
| 12 | 1 day | α Strep not Enterococcus<br>α Strep not Enterococcus 2nd strain<br>Staphylococcus, coag.-<br>Staphylococcus, coag.- 2nd strain<br>Gram+ bacillus<br>Gram+ bacillus 2nd strain<br>Candida albicans | 200 µg/ml | .0075% | 4 | 2 | 2 |
| 13 | 1 day | Staphylococcus, coag.-<br>α Strept<br>α Strept<br>γ Strep not Enterococcus<br>Gram+ cocc<br>Gram+ bacillus<br>Candida albicans | 200 µg/ml | .0075% | 4 | 4 | 4 |
| 14 | 6 days | α Strep not Enterococcus<br>Staphylococcus, coag.-<br>Gram+ cocc<br>Gram+ cocc<br>Staphylococcus, coag.- | 200 µg/ml | .0075% | 4 | 0 | 0 |
| 15 | 1 day | α Strep not Enterococcus<br>α Strept not Enterococcus 2nd strain<br>α Strep not Enterococcus 3rd strain<br>α Strep not Enterococcus<br>Streptococcus Group B<br>Staphylococcus, coag.-<br>Gram+ cocc<br>Gram+ bacillus, res. Corynebacterium<br>Haemophilus species | 200 µg/ml | .0075% | 4 | 1(1) | 2(7) |
| 16 | 1 day | Staphylococcus aureus<br>α Strept<br>Gram+ cocc<br>Micrococcus species<br>Haemophilus species<br>Haemophilus species 2nd strain<br>α Strept<br>γ Strept<br>Gram+ bacillus<br>Gram+ bacillus | 200 µg/ml | .0075% | 4 | 1(5) | 0 |
| 17 | 1 day | Staphylococcus, coag.<br>Gram+ bacillus, res. Corynebacterium<br>α Strept not Enterococcus | 200 µg/ml | .0075% | 4 | 0 | 0 |

Qualitative Colony Count

| | |
|---|---|
| 4 = | 301+ |
| 3 = | 101-300 |
| 2 = | 6-100 |
| 1 = | 1-5 col. |
| 0 = | 0 |

[Bacterial]: McF 0.5 (1.5×10⁸/mL)
total vol.: 1 mL
incubate t: 10 min.
irrad. vol.: 0.05 mL
media: tube
agar: Std. Plate Ct.
temp: 37° C
incubate t: 24 hrs.

| Nr. | Description | pH | MB [conc.] | MB volume | Saline volume | Bacterial Volume | Power | Dose | Light Rate | Dose Time | Results L− | L+ |
|---|---|---|---|---|---|---|---|---|---|---|---|---|
| 1 | Staph. aureus+MB | 5.78 | 25 µg/mL | 0.04 mL | 0.76 mL | 0.2 mL | 0.71 W | 60 J/cm² | 150 mW | 400 sec. | 4 | 1 (5) |
| 2 | " | 7.55 | " | " | " | " | " | " | " | " | 4 | 0 |
| 3 | " | 8.2 | " | " | " | " | " | " | " | " | 4 | 1 (1) |
| 4 | Staph. aureus+MB | 5.78 | 10 µg/mL | 0.016 mL | 0.784 mL | 0.2 mL | 0.71 W | 60 J/cm² | 150 mW | 400 sec. | 4 | 0 |
| 5 | " | 7.55 | " | " | " | " | " | " | " | " | 4 | 0 |
| 6 | " | 8.2 | " | " | " | " | " | " | " | " | 4 | 0 |
| 7 | Pseudo. aeurg+MB | 5.78 | 50 | 0.078 | 0.722 | " | " | " | " | " | 4 | 0 |
| 8 | " | 7.55 | " | " | " | " | " | " | " | " | 4 | 0 |
| 9 | " | 8.2 | " | " | " | " | " | " | " | " | 4 | 0 |
| 10 | Staph. aureus+MB | 5.78 | 7 µg/mL | 0.01 mL | 0.79 mL | 0.2 mL | 0.1 W | 20 J/cm² | 127 mW | 157 sec. | 4 | 4 |
| 11 | " | 7.55 | " | " | " | " | " | " | " | " | 4 | 2 (9) |
| 12 | " | 8.2 | " | " | " | " | " | " | " | " | 4 | 2 (6) |
| 13 | Pseudo. aeurg+MB | 5.78 | 32 | 0.05 | 0.75 | " | " | " | " | " | 4 | 4 |
| 14 | " | 7.55 | " | " | " | " | " | " | " | " | 4 | 4 |
| 15 | " | 8.2 | " | " | " | " | " | " | " | " | 4 | 4 |
| 16 | Staph. aureus+MB | 5.78 | 10 µg/mL | 0.0156 mL | 0.785 mL | 0.2 mL | 0.1 W | 20 J/cm² | 127 mW | 157 sec. | 4 | 4 |
| 17 | " | 7.55 | " | " | " | " | " | " | " | " | 4 | 0 |
| 18 | " | 8.2 | " | " | " | " | " | " | " | " | 4 | 0 |
| 19 | Pseudo. aeurg+MB | 5.78 | 50 | 0.078 | 0.722 | " | " | " | " | " | 4 | 1 (3) |
| 20 | " | 7.55 | " | " | " | " | " | " | " | " | 4 | 2 (66) |
| 21 | " | 8.2 | " | " | " | " | " | " | " | " | 4 | 2 (24) |
| 22 | Staph. aureus+MB | 5.78 | 8.5 µg/mL | 0.0133 mL | 0.787 mL | 0.2 mL | 0.1 W | 20 J/cm² | 127 mW | 157 sec. | 4 | 3 |
| 23 | " | 7.55 | " | " | " | " | " | " | " | " | 4 | 1 (20) |
| 24 | " | 8.2 | " | " | " | " | " | " | " | " | 4 | 0 |
| 25 | Pseudo. aeurg+MB | 5.76 | 50 | 0.078 | 0.722 | " | " | " | " | " | 4 | 0 |
| 26 | " | 7.55 | " | " | " | " | " | " | " | " | 4 | 2 (14) |
| 27 | " | 8.2 | " | " | " | " | " | " | " | " | 4 | 2 (35) |

*FIG. 5*

PHOTODYNAMIC CELLULAR AND ACELLULAR ORGANISM ERADICATION UTILIZING A PHOTOSENSITIVE MATERIAL AND SURFACTANT

RELATED APPLICATIONS

This application claims the benefit of priority, pursuant to 35 U.S.C. §119-120, from copending application Ser. Nos. 09/139,866 filed Aug. 25, 1998, and 09/514,070 filed Feb. 26, 2000.

FIELD OF THE INVENTION

The invention relates to a photodynamic therapy (PDT) or process, and more particularly to a photodynamic therapy or process utilizing a photosensitive material and a chemical agent, such as a surfactant material, for in vitro and in vivo cellular and acellular organism eradication. The invention also relates to photodynamic eradication of bacteria, fungal, and viral wound infections and sterilization of tissue using a photosensitive material, such as methylene blue or toluidene blue, and a surfactant material, such as polymyxin B, SDS, or cetrimide. Additionally, the invention relates to photodynamic eradication of cancer cells, such as present within a tumor, by PDT in conjunction with a photosensitive material and a surfactant. The present invention advantageously uses light energy in combination with a photosensitive material and a surfactant material to treat both in vitro and in vivo pathogens, including cancer cells and microbiological pathogens. The invention also relates to the eradication or destruction of biofilms via a photodynamic mechanism. The invention further relates to the eradication of spores in both in vivo and in vitro applications.

BACKGROUND OF THE INVENTION

Abnormal cells and acellular organisms are known to selectively absorb certain dyes (photosensitive materials) delivered to a treatment site to a more pronounced extent than surrounding tissue. Once presensitized, abnormal cells or acellular organisms can be destroyed by irradiation with light of an appropriate wavelength corresponding to an absorbing wavelength of the photosensitive material, with minimal damage to surrounding normal tissue. This procedure, which is known as photodynamic therapy (PDT), has been clinically used to treat metastatic breast cancer, bladder cancer, head and neck cancers, and other types of malignant tumors.

U.S. Pat. No. 5,676,959 to Heitz et al., purportedly discloses an ingestible phototoxic insecticidal composition including a photoactive dye, an attractant compound and/or feeding stimulant, and an adjuvant, whereby the adjuvant interacts with the photoactive dye and insect gastrointestinal (GI) tract to facilitate transport of the phototoxic insecticide across the GI tract. The use of an adjuvant to facilitate pharmaceutical uptake via GI tract absorption is known in the art. Unlike the surface acting agents of the Applicant's present invention, these adjuvants do not produce a disorientation of a cell membrane so that the cell membrane no longer functions as an effective osmotic barrier.

The article "Inactivation of Gram-Negative Bacteria by Photosensitized Porphyrins" by Nitzan, et al., published in Photochemistry and Photobiology, Vol. 55, No. 1, pp. 89-96, 1992, purportedly discloses the use of polycationic agent polymyxin nonapeptide (PMNP) in association with a photoactive agent, deuteroporphyin (DP). PMNP is disclosed to disturb the outer membrane of a gram-negative bacteria so as to permit access of the DP to bind to the internal lipoprotein osmotic membrane of the bacterial cell. PMNP is disclosed to only disturb the outer membrane structure and not its function, and not cause metabolic leakage from the cells (or osmotic changes in the cell). Unlike the surface acting agent of the Applicant's present invention, PNMP does not produce a disorientation of a cell membrane so that the cell membrane no longer functions as an effective osmotic barrier. In the Applicant's present invention, the surface acting agent causes a disorientation of the cell membrane thereby compromising the effective osmotic membrane barrier and thus allowing the photosensitizer to diffuse through the compromised cell membrane into the cell.

U.S. Pat. No. 5,616,342, to Lyons, purportedly discloses an emulsion comprising a lipid, a poorly water-soluble photosensitizing compound, a surfactant, and a cosurfactant. Poorly water-soluble photosensitizers are disclosed to pose serious challenges to achieving suitable formulation for administration to the body. Lyons '342 discloses that surfactants facilitate the preparation of the emulsion by stabilizing the dispersed droplets of an oil-in-water emulsion, and that the use of surfactants in combination with poorly water-soluble pharmacologic compounds is known in the art. Unlike the surface acting agents of the Applicant's present invention, the surfactant in Lyons does not produce a disorientation of a cell membrane so that the cell membrane no longer functions as an effective osmotic barrier.

SUMMARY OF THE INVENTION

The present invention provides a method of photoeradication of cells and acellular organisms, such as during an in vitro or in vivo disinfection or sterilization procedure, or for cancer cell or acellular organism eradication. In one embodiment, the method utilizes a combination of a photosensitive material and a chemical agent, such as a surfactant material, in a solution. The invention additionally provides a method of dispensing a combined solution at or near the tissue site and subsequently irradiating the tissue site with light at a wavelength absorbed by the photosensitive material. The invention also relates to an apparatus or kit assembly including a surfactant material and a photosensitive material. Yet another aspect of the present invention is the eradication or destruction of biofilms via a photodynamic mechanism.

The invention also relates to a use of a photosensitizing material, such as methylene blue or toluidene blue, in combination with a surfactant compound, such as polymyxin B, SDS or cetrimide, in a PDT treatment protocol against bacterial, fungal, acellular organism infections, and/or for cancer cell photoeradication. A treatment device is configured to deliver light energy to the area of infection or cancer cell activity at wavelengths ranging from about 450 nm to about 850 nm; provide a dosage rate ranging from about 0 to about 150 mw/cm$^2$; and provide a light dose ranging from 0 to about 300 J/cm$^2$.

The use of a photosensitive material, such as methylene blue or toluidene blue, combined with a surfactant material, such as SDS, polymyxin B, or cetrimide, in a photodynamic therapy advantageously acts as a broad spectrum antimicrobial, i.e., antibacterial, antiviral, sporicidal, and/or antifungal agent. The photosensitizer/surfactant combination and PDT may be used, for example, before a surgical operation. The present invention advantageously results in the destruction of gram positive and gram negative bacteria and fungus. Importantly, the present invention acts to destroy antibiotic resistant bacteria as it utilizes a different destruction mechanism than antibiotics.

The invention also relates to a method of treating an infection including identifying an in vivo area of infection; applying or dispensing a concentration including a photosensitive material, such as methylene blue or toluidene blue, and a surfactant, such as polymyxin B, SDS, or cetrimide, to the area of infection; and exposing the area of infection with a light having a light wavelength, light dosage and a light dosage rate. For toluidene blue, the light wavelength may range from about 610 nm to about 680 nm. For methylene blue, the wavelength may range from about 630 nm to about 664 nm. The light dosage may range from about 10 $J/cm^2$ to about 60 $J/cm^2$. The light dosage rate may range from about 50 $mw/cm^2$ to about 150 $mw/cm^2$. The concentration for methylene blue and toluidene blue may range from about 10 μg/ml to about 500 μg/ml. For other photosensitive materials, the preferred wavelength or range may be known or available. The area of infection may include gram positive and gram negative bacteria, fungus, spores, or viruses including, but not limited to, at least one of *Staphylococcus* sp., *Candida albicans, Escherichia coli, Enterococcus* sp., *Streptococcus* sp., *Pseudomonus aeruginosa, Hemophilus influenzae, Clostridia* sp., Herpes strains, or human immunodeficiency virus (HIV).

The invention also relates to a treatment kit having a solution including at least a combination of a photosensitizing material, such as methylene blue or toluidene blue, and a surfactant material, such as polymyxin B, SDS, or cetrimide. For polymixin B, the concentration ranges may be from about 3 μg/ml to about 500 μg/ml. For SDS and cetrimide, the concentration range may be from 0.005% to 1%. A laser light emitting treatment device may be utilized to effect the photodynamic process, including but not limited to a light source which emits at wavelengths ranging from about 450 nm to about 850 nm; providing a dosage rate ranging from about 0 to about 150 $mw/cm^2$; and providing a light dose ranging from 0 to about 300 $J/cm^2$. Alternative light sources would also be practicable as appreciated by one skilled in the relevant arts.

The invention also relates to a method of treating an infection, an in vitro or in vivo sterilization procedure, or photo-eradication of cancer cells, including the steps of providing one or more cells; providing a concentration of combined photosensitive material/surfactant on or near the one or more cells; and applying a light having a wavelength ranging from about 450 nm to about 850 nm; a dosage rate ranging from about 0 to about 150 $mw/cm^2$; and a light dose ranging from 0 to about 300 $J/cm^2$ to the one or more cells wherein the combination of light and photosensitive material is adapted to cause photodestruction of the one or more cells. The one or more cells may be an infection caused by or associated with a bacteria, virus, or fungus. Alternatively, the one or more cells may be cancer cells. Virus infected cells may also be treated in accordance with the present invention. In such instance, a virus within the cell may be specifically eradicated without destruction of the host cell. Obligate intracellular bacterial agents, such as *Chlamydia, Rickettsia*, and *Ehrlichia*, may be treated in accordance with the present invention. Other bacteria may also be treated in accordance with the present invention. The one or more cells may be gram positive or gram negative bacteria. The photosensitive material may be methylene blue, toluidene blue, or a combination thereof. The photosensitive material may be monomeric, dimeric, or polymeric.

Another aspect of the present invention is the provision of biofilm reduction and/or eradication. A biofilm is an accumulation of microorganisms including bacteria, fungi and viruses that are embedded in a polysaccharide matrix and adhere to solid biologic and non-biologic surfaces. Biofilms are medically important as they may account for a majority of microbial infections in the body. Biofilms account for many of the infections of the oral cavity, middle ear, indwelling catheters and tracheal and ventilator tubing. The National Institutes of Health estimates that the formation of biofilms on heart valves, hip and other prostheses, catheters, intrauterine devices, airway and water lines and contact lenses has become a $20 billion dollar health problem in the United States. A treatment apparatus and protocol for the reduction and/or eradication of biofilms is another aspect of the present invention.

Biofilms are remarkably resistant to treatment with conventional topical and intravenous antimicrobial agents. The Center for Biofilm Engineering at Montana State University has reported that biofilms may require 100 to 1,000 times the standard concentration of an antibiotic to control a biofilm infection. This is thought to be due to the antibiotic's inability to penetrate the polysaccharide coating of the biofilm. Even more concerning is that biofilms increase the opportunity for gene transfer due to the commingling of microorganisms. Such gene transfer may convert a previous avirulent commensal organism into a highly virulent and possibly antibiotic resistant organism.

Bacteria embedded within biofilms are also resistant to both immunological and non-specific defense mechanisms of the body. Bacterial contact with a solid surface triggers the expression of a panel of bacterial enzymes that cause the formation of polysaccharides that promote colonization and protection of the bacteria. The polysaccharide structure of biofilms is such that immune responses may be directed only at those antigens found on the outer surface of the biofilm and antibodies and other serum or salivary proteins often fail to penetrate into the biofilm. Also, phagocytes may be effectively prevented from engulfing a bacterium growing within a complex polysaccharide matrix attached to a solid surface.

Nosocomial pneumonia is the most prevalent infection in patients who are mechanically ventilated. It is the leading contributor to mortality in patients, accounting for 50% of deaths in patients with hospital acquired infections. The endotracheal tubes (ET) and tracheostomy tubes have long been recognized as a risk factor for nosocomial pneumonia since they bypass host defenses allowing bacteria direct access to the lungs. These tubes are commonly made of polyvinyl chloride, a surface on which local bacteria colonize rapidly to form an adhesive polysaccharide glycocalyx layer. This glycocalyx layer protects bacterial colonies from both natural and pharmacologic antibacterial agents, in effect increasing the virulence of the bacterial species in the intubated host. This phenomenon of biofilm formation has been demonstrated to occur on ET tubes and subsequent dislodgement of biofilm protected bacteria in the lungs by a suction catheter is considered to be a significant factor in the pathogenesis of nosocomial pneumonia. Indeed, in a study of biofilm formation in endotracheal tubes, microbial biofilm was identified by surface electron microscopy in 29 of 30 endotracheal tubes examined. Interestingly, there was no biofilm formation on the outer surface of the ET tube. Biofilm formed exclusively on the luminal surface of all tubes regardless of whether the patients had received broad spectrum antibiotics and was most prevalent around the side hole of the tip region. ET tubes obtained within 24 hours of placement showed large areas of surface activity with adherent bacteria in a diffuse pattern indicating initial colonization of the ET tube. The surface of tubes in place for longer periods had a profuse microbial biofilm. In some instances a large mass of matrix enclosed bacterial cells appeared to project from the confluent accretion on the luminal surface of the ET tube in such a manner that it could be dislodged readily and aspirated into the lower respiratory tract. Pseudomonas species, *Staphylococcus aureus*, and enteric aerobic bacteria including *E. coli*, were the most frequently isolated pathogens in the ET tubes in patients that did not receive broad spectrum antibiotics. These also are the pathogenic bacteria most commonly found in nosocomial pneumonia. In patients that received broad spectrum antibiotics yeast species and *Streptococcus* species were more common.

Evaluations have been made into the relationship of biofilm formation in endotracheal tubes and distant colonization of the pulmonary tree. These evaluations have demonstrated that bacteria from the endotracheal tube biofilm were capable of being cultured from the moisture exchanger and the ventilator tubing up to 45 cm from the tip of the endotracheal tube. Furthermore they demonstrated that contamination of the tracheal tube biofilm with a patient's own gastrointestinal flora provides a mechanism for initial and repeated lung colonization and secondary pneumonia. These life threatening pulmonary infections are perpetuated by microbiological seeding from the tracheostomy and endotracheal tube biofilms and become difficult to treat due to the propensity of the biofilm microorganisms to develop antibiotic resistance.

Methylene blue (MB) based photodynamic therapy has been demonstrated in vitro and in vivo to be effective in the photoeradication of antibiotic resistant gram positive and gram negative bacteria. Methylene blue has a very low tissue toxicity and can be administered to humans orally and intravenously in high doses without any toxic effects. Because of the known low toxicity and its present use and acceptance in medical practice as well as its high photoactive potential this photosensitive material is ideal use in accordance with the present invention for evaluation of its effect on the destruction of bacteria, viruses and fungi. The photoactive dye Methylene blue belongs to the phenothiazine class. Its bactericidal effect is related to its photodynamic properties. This dye is a single pure compound and has a strong absorption at wavelengths longer than 620 nm, where light penetration into tissue is optimal. The absorbance peak of MB is at 664 nm, its optical extinction coefficient is 81 600 $M^{-1}$ $cm^{-1}$.

The photoactivity of MB results in two types of photooxidations: (i) direct reaction between the photoexcited dye and substrate by hydrogen abstraction or electron transfer creating different active radical products; and (ii) direct reaction between the photoexcited dye in triplet state and molecular oxygen producing singlet oxygen. Both kinds of active generated products are strong oxidizers and they cause cellular damage, membrane lysis, protein inactivation and/or DNA modification.

MB has a high quantum yield of the triplet state formation (~T=0.52-0.58) and a high yield of the singlet oxygen generation (0.2 at pH 5 and 0.94 at pH 9).

Biofilms are resistant to topical, oral and intravenous antibiotic administration due to the polysaccharide glycocalyx formation that surrounds the bacteria. The polysaccharide coating prevents the antibiotic from penetrating into the biofilms and destroying the bacteria. Methylene blue has the potential ability to destroy biofilms as it selectively binds and penetrates polysaccharides thereby exposing the bacteria in the biofilm to the photodestructive effects of methylene blue. For this reason, methylene blue may be an ideal photosensitizer that may provide a means for the broad spectrum photoeradication of biofilms. The use of a surfactant, such as SDS, can act to both emulsify the biofilm and increase a membrane permeability of an acellular or cellular organism within the biofilm. The combination of a surfactant with a photosensitive material permits the photosensitive material to pass through the biofilm and acellular or cellular organism membrane, and accumulate within the acellular or cellular organism. As a result, a treatment protocol according to the present invention may result in more effective eradication of acellular and cellular organisms within biofilms.

Another object of the present invention is the provision of a treatment protocol utilizing a photosensitive material and surfactant in a pH-selective solution. By adjusting the pH of the solution, an enhanced kill rate of gram-negative or gram-positive bacteria results. The pH of the solution can be determined and adjusted using known processes or agents.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawings and description are to be regarded as illustrative in nature, and not as restrictive.

BRIEF DESCRIPTION OF THE FIGURES

FIG. 2 is a table of results of photodynamic eradication using a combined solution of methylene blue and the surfactant, SDS.

FIG. 3 is a table of results of photodynamic eradication using methylene blue and SDS in the treatment of oral candidiasis.

FIG. 4A is first page of a table of results of photodynamic eradication of biofilm microorganisms using a photosensitive material and the surfactant.

FIG. 4B is second page of a table of results of photodynamic eradication of biofilm microorganisms using a photosensitive material and the surfactant.

FIG. 5 is a table of results of photodynamic eradication using a pH variable solution of a photosensitive material.

DETAILED DESCRIPTION OF THE INVENTION

Figure 1:
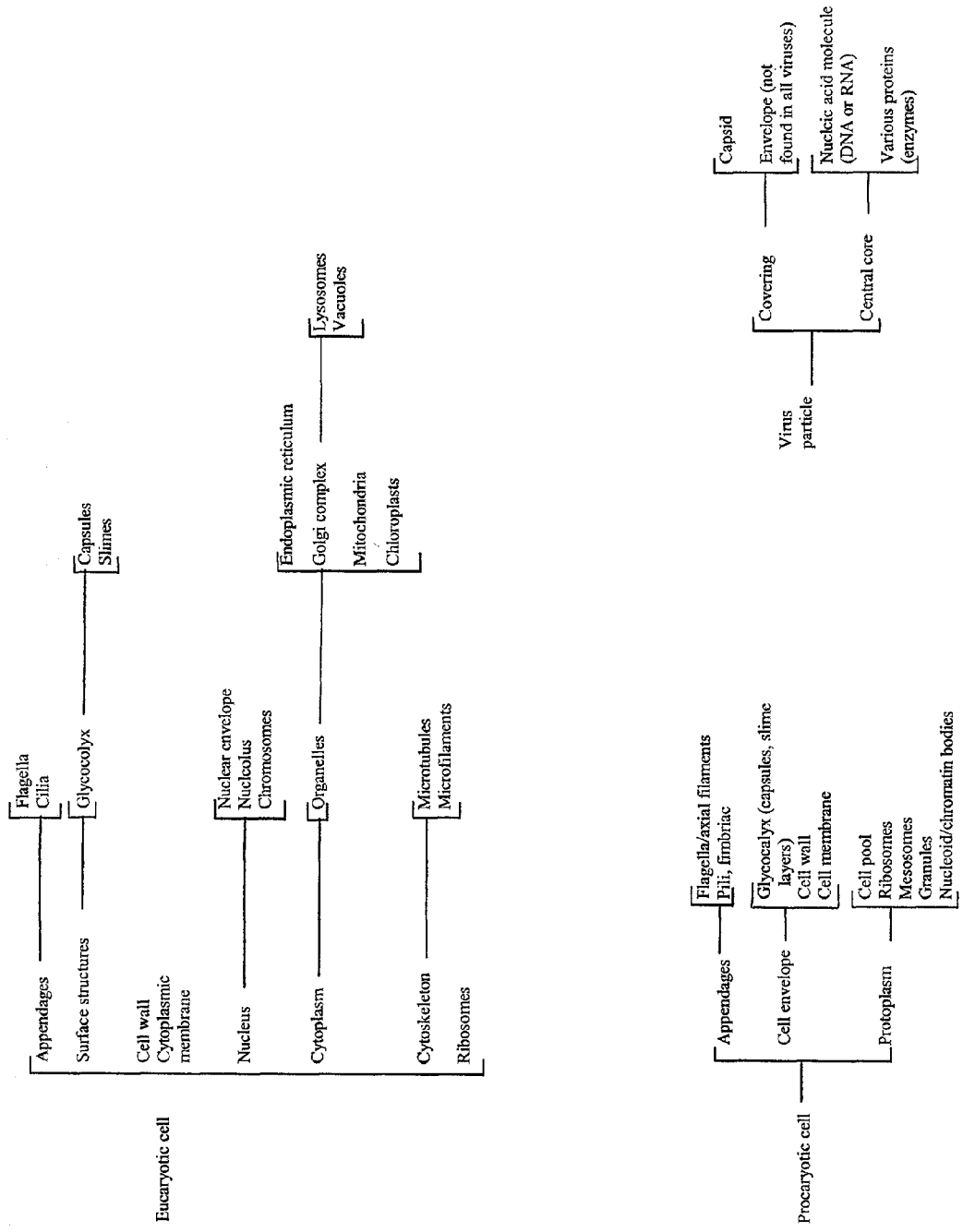
FIG. 1 is a tree structure of organisms.

In accordance with the invention, a photodynamic therapy utilizes a photosensitive material, such as methylene blue or toluidene blue, in combination with a chemical agent, such as surface acting agent or 'surfactant', and a light emitting device, such as a light wand, light patch, light pad or shaped light-emitting article such as a mouthpiece to illuminate the site. The photodynamic therapy according to the present invention may be utilized in the eradication of cellular organisms, such as tumor cells, cancer cells, virus-infected cells, bacteria, etc. The photodynamic therapy according to the present invention may also be utilized in the eradication of acellular organisms, defined broadly to include organisms not composed of cells, e.g., bodies of protoplasm made discrete by an enveloping membrane (also referred to a capsule, envelope, or capsid). Examples of acellular organisms include, but are not limited to, viruses, spores, and other virus-like agents such as viroids, plasmids, prions, and virinos, and other infectious particles.

Reference may be made to FIG. 1, wherein component structures of acellular and cellular organisms are presented. Procaryotic cells are cellular organisms, including bacteria. The component structures of procaryotic cells include appendages, cell envelope, and protoplasm. The cell envelope further includes the glycocalyx (capsules, slime layers), cell wall, and cell membrane. All bacteria cells invariably have a cell envelope, glycocalyx, cell membrane, cell pool, ribosomes, and a nucleoid; the majority have a cell wall. Although they are common to many species, flagella, pili, fimbriae, capsules, slime layers, and granules are not universal components of all bacteria. Organisms of the genera *Chlamydia*, *Rickettsia*, and *Ehrlichea*, referred to as obligate intracellular bacteria, are prokaryotes that differ from most other bacteria with respect to their very small size and obligate intracellular parasitism.

Eucaryotic cells are typical of certain microbial groups (fungi, algae, protozoans, and helminth worms) as well as all animal and plant cells. Eucaryotic cells have component structures including appendages, surface structures, cell wall, cytoplasmic membrane, nucleus, cytoplasm, cytoskeleton, and ribosomes. The surface structures may include glycocalyx, capsules, and slimes. Virus particles are not cells and they neither possess procaryotic nor eucaryotic structural qualities. Instead, they are large, complex macromolecules, with parts made up of repeating molecular subunits. Virus particles include component structures of a covering and a central core. The covering includes a capsid and in some viruses, an envelope. All viruses have a protein capsid or shell that surrounds the nucleic acid strand. Members of 12 of the 17 families of animal viruses possess an additional covering external to the capsid called an envelope, which is actually a modified piece of the host's cell membrane. Viruses that lack this envelope are considered naked nucleocapsids. Special virus-like infectious agents include the prion (proteinacious infectious particles) and viroids.

A photosensitive material is defined herein as a material, element, chemical, solution, compound, matter, or substance which is sensitive, reactive, receptive, or responsive to light energy. Photosensitive materials may be provided in a liquid, gaseous, or solid form, including but not limited to liquids, solutions, topical ointments, or powders. Photosensitive materials for use in accordance with the present invention are generally non-toxic to the target cellular or acellular organisms and surrounding tissues at concentrations envisaged. However, there is no particular requirement that the photosensitive material should be non-toxic to the microbes. Particular photosensitizers which may be used in accordance with the invention include dyes and compounds such as methylene blue and toluidene blue.

The terms "chemical agent" and "surface acting agents" and "surfactants" as used herein are broadly defined to include materials, compounds, agents, chemicals, solutions, or substances which alter the energy relationships at molecular interfaces. Among the manifestations of these altered energy relationships is the lowering of surface or interfacial tensions. Chemical agents or compounds displaying surface activity are characterized by an appropriate structural balance between one or more water-attracting groups and one or more water-repellent groups. Surfactants are characterized by having two different moieties, one polar and the other nonpolar. The polar moeity is referred to as hydrophilic or lipophobic, and the nonpolar as hydrophobic or lipophilic. The electrical charge on the hydrophilic portion of a surface acting agent may serve as a convenient basis of classification of these compounds. Surface active agents have been classified as: Anionic, Cationic, Non-Ionic, and Amphoteric. Other classes of surfactants are also known or may be developed or defined in the future. Chemical agents, such as surfactants, are known to affect the permeability of cell membranes, and membrane-like structures of acellular organisms, such capsids and envelopes. The ability of these chemical agents or surfactants to become oriented between lipid and protein films is thought to produce a disorientation of the membrane of microorganisms, so that it no longer functions as an effective osmotic barrier. The term 'membrane' as used herein is meant to broadly include cellular or acellular organism structures, such as cell walls, cytoplasmic membranes, cell envelopes, coverings, capsids, envelopes, or other types of boundary-defining terms of cellular or acellular organisms. It is believed that a photosensitive material may diffuse through the membrane of a microorganism having a surfactant-compromised membrane. A photosensitive material concentration within the membrane and the organism increases over time via osmotic diffusion of the photosensitive material across the surfactant-compromised membrane. The polymixins, colisimethate, and the polyene antifungal agents nystatin and amphotericin are surfactants, as is sodium dodecyl sulfate (SDS). Cetrimide is also a known surfactant.

A light source is utilized to practice embodiments of the present invention. The light source may be laser light source, a high intensity flash lamp, or other illumination sources as appreciated by those skilled in the relevant arts. A broad spectrum light source may be utilized, however a narrow spectrum light source is one preferred light source. The light source may be selected with reference to the specific photosensitive material, as photosensitive materials may have an associated range of photoactivation. A laser light source may be used to practice the present invention. A variety of laser light sources are currently available, and the selection of a particular laser light source for implementing the PDT would readily be appreciated by those skilled in the relevant arts. A hand manipulable light wand or fiber optic device may be used to illuminate tissue within a living body. Such fiber optic devices may include a disposable fiber optic guide provided in kit form with a solution containing a photosensitive material and a surfactant. Other potential light devices for use in accordance with the present invention include the devices disclosed in applicant's U.S. Pat. No. 6,159,236, entitled Expandable treatment device for photodynamic therapy and method of using same, and U.S. Pat. No. 6,048,359, entitled Spatial orientation and light sources and method of using same for medical diagnosis and photodynamic therapy, both incorporated in their entireties by reference herein. The laser source may be selected with regard to the choice of wavelength, beam diameter, exposure time and sensitivity of the cellular and/or acellular organisms to the laser/photosensitizer/surfactant combination. In preferred embodiments, the light source is utilized for a period of time necessary to affect a photodynamic response. The period of time for photodynamic activation of the photosensitive material is preferably between 5 seconds and 1 hour. Yet more preferably, the period of time for light illumination is between 2 and 20 minutes.

Repeat administrations of a treatment protocol may also be necessary or desired, including repeat administrations of surfactants and photosensitive materials and light activation. The repeat administrations may include different surfactants and/or photosensitive materials than previously administered. Repeat administrations of the treatment protocol may continue for a period of time.

Additional aspects of the present invention include administration or delivery approaches of the photosensitive material and the chemical agent or surfactant. In one example, the photosensitive material and the surfactant are provided in a combined solution and topically applied to the cell site. In alternative embodiments, the photosensitive material may be applied or delivered or dispensed to a tissue site before, during, or after the application or delivery of the surfactant through known delivery/administration approaches. In one preferred embodiment, a topical surfactant application would precede a topical photosensitive material application by 1-30 minutes.

Additional aspects of the present invention further include combinations of different photosensitive materials and different chemical agents or surfactants during a treatment protocol. In one preferred embodiment, a particular combination of a photosensitizer and a surfactant would be dispensed to the tissue site in association with a first photodynamic illumination of the tissue site. After a period of time, another different particular combination of a photosensitizer and a surfactant would be dispensed to the tissue site in association with a second photodynamic illumination of the tissue site.

Yet other aspects of the invention include combining a plurality of different surfactants with a given photosensitive material, and/or combining a plurality of different photosensitive materials with a given surfactant.

In another preferred embodiment, a photosensitive material such as methylene blue or toluidene blue may be used in combination with surfactants, such as SDS, polymyxin B, Arguard™, and/or cetrimide, and activated by light energy to provide broad spectrum antibiotic activity for destroying both gram positive and gram-negative bacteria, funguses, viruses, spores, and/or cancer cells. The photosensitive material and surfactant may be combined in solution and administered to a site to be treated. Solution administration may include topical application, or intravenous, subcutaneous, intratumoral, or peritumoral injection. Additional administration approaches may also be practicable. An intratumoral injection of the solution may be advantageous for photoeradication of tumor cells.

One particular treatment protocol according to the present invention utilizes the photosensitive material methylene blue and surfactant SDS. SDS concentrations from 0.001% to 0.01% have been identified as advantageous in the destruction of certain microorganisms, such as *Candida albicans, Escherichia coli, Pseudomonas aeruginosa, Staphylococcus aureus*, and *Streptococcus pneumoniae*. Reference may be made to FIG. 2, which illustrates a schedule of results for an investigation according to the present invention. The inquiry was made into photoeradication using methylene blue mediated PDT and the surfactant SDS, at a wavelength of approximately 664 nm. The laser used for illumination was a diode laser. Methylene blue concentrations ranged from 5 to 100 µg/ml. SDS concentrations ranged from 0.003 to 0.01%. Light power ranged from 0.127 to 0.3 watts. The combined solution was topically applied at the cell site. Light dosage rates ranged from 75 to 100 mw/cm2. Light dosages ranged from 15 to 60 J/cm2. A qualitative colony count relates particular colony counts to an associated score. For instance, a qualitative colony count of 5 would yield a score of '1', while a colony count of 151 would have an associated score of '3'. The results of this investigation demonstrated that the solution including a surfactant and a photosensitising agent sensitized several species of bacteria to killing by laser irradiation. As a result, one particularly efficacious treatment for eradicating a microorganism according to the present invention may include the steps of disposing a solution containing a methylene blue and SDS at a tissue site and illuminating the tissue site with a light source effective to initiate a photodynamic therapy.

Reference may also be made to FIG. 3, which illustrates a schedule of results for an investigation according to the present invention. The inquiry was made into photoeradication of oral Candidiasis in immunosuppressed mice using methylene blue mediated PDT and the surfactant SDS, at a wavelength of approximately 664 nm. Methylene blue concentrations ranged from 50 to 300 µg/ml. SDS concentrations ranged from 0 to 0.0075%. The combined solution was topically applied at an oral cell site. Light dose was 275 J/cm. Light dose rate was 400 mW/cm. Time of illumination was 687.5 sec. Cultures were assessed: (i) without solution and light (M−L−), (ii) with solution and without light (M+L−), and (iii) with solution and light (M+L+). A qualitative colony count relates particular colony counts to an associated score. For instance, a qualitative colony count of 5 would yield a score of '1', while a colony count of 151 would have an associated score of '3'. The results of this investigation demonstrated that the solution including a surfactant and a photosensitising agent sensitized oral candidiasis to killing by laser irradiation. As a result, an efficacious treatment for eradicating *Candida albicans*, the organism that causes oral candidiasis, would include the steps of disposing a solution containing a methylene blue and SDS at an oral tissue site and illuminating the tissue site with a light source effective to initiate a photodynamic therapy. Additionally, this study revealed that a preferred concentration of methylene blue was 200 µg/ml.

In addition to methylene blue and toluidene blue as described above, known photosensitive materials which may find applicability in practicing the present invention include, but are not limited to, the following:

| PHOTOSENSITIVE MATERIAL | WAVELENGTH |
|---|---|
| Hypiricin | 550-660 nm |
| Aluminum phthalocyanine | 670-675 nm |
| Merocyanine | 500-560 nm |
| Psoralen | 320-400 nm |
| Rose Bengal | 548 nm |
| Acridine orange | 489 nm |
| Indocyanine green | 660 nm |
| Nile blue | 628 nm |
| Nile red | 553 nm |
| Toluidene | 630-660 nm |
| Methylene green | 620-660 nm |
| Lutetium Texaphyrin | 732 nm |
| Benzporphyrin derivative | 690 nm |
| Foscan (mTHPC) | 652 nm |
| Tin ethyl etiopurpurin | 664 nm |
| Photofrin (porfimer solution) | 630 nm |

Another aspect of the present invention is the provision of biofilm reduction and/or eradication. A biofilm is an accumulation of microorganisms including bacteria, fungi and viruses that are embedded in a polysaccharide matrix and adhere to solid biologic and non-biologic surfaces. Biofilms are medically important as they may account for a majority of microbial infections in the body. Biofilms account for many of the infections of the oral cavity, middle ear, indwelling catheters and tracheal and ventilator tubing.

SDS has been used in oral medications and has a very low toxicity when administered orally or topically. The use of a surfactant, such as SDS, in combination with a photosensitive material, such as methylene blue, is useful in treating biofilms. It is believed that by penetrating and emulsifying the protective glycocalyx and allowing the photosensitive material to penetrate into the biofilm and accumulate proximate to the embedded microorganisms, an increased diffusion of the photosensitizer into the microorganisms may be achieved. An increase in the diffusion rate is further believed to facilitate a broad spectrum photodestruction of the biofilm and/or embedded microorganisms.

Biofilms are a serious and ever increasing health problem with limited ability at this time to effectively treat them. The development of a prototype topical MB, SDS and light application system for the prevention and/or photoeradication of biofilms in endotracheal tubes, tracheostomy tubes, airway lines and indwelling catheters would greatly impact and reduce both the significant rate of nosocomial pneumonias and other catheter related infections but also reduce the ever increasing rate of antimicrobial resistance. As a result, one particularly efficacious treatment for eradicating a microorganism of a biofilm according to the present invention may include the steps of disposing a solution containing a methylene blue and SDS at a tissue site and illuminating the tissue site with a light source effective to initiate a photodynamic therapy.

FIGS. 4A and 4B illustrate a schedule of results for a biofilm microorganism eradication of endotracheal tubes. The inquiry was made into photoeradication using methylene blue mediated PDT and the surfactant SDS, at a wavelength of approximately 664 nm. Methylene blue concentrations ranged from 100 to 250 µg/ml. SDS concentrations ranged from 0.003% to 0.0075%. Light dose was 100 J/cm. Light dose rate was 400 mW/cm. Time of illumination was 250 sec. Cultures were assessed: (i) without light (L−), (ii) with a first application of light (L+), and (iii) with a first and second applications of light (L++). A qualitative colony count (as in FIGS. 2 and 3) relates particular colony counts to an associated score. For instance, a qualitative colony count of 5 would yield a score of '1', while a colony count of 151 would have an associated score of '3'. The results of this investigation demonstrated that the solution including a surfactant and a photosensitising agent sensitized several organisms to killing by laser irradiation, including antibiotic resistant organisms. As a result, an efficacious treatment for biofilm microorganisms would include the steps of disposing a solution containing a photosensitive material, such as methylene blue, and a surfactant, such as SDS, upon the biofilm and illuminating the biofilm with a light source effective to initiate a photodynamic therapy.

Another treatment protocol utilizing the photosensitizer methylene blue and cetrimide has been identified as advantageous in the destruction of certain microorganisms, particularly spores or spore like organisms produced by various bacteria including *Bacillus subtillus, Bacillus anthrax, Mycobacterium tuburculosis* and *Clostridia*.

Another preferred embodiment of the present invention provides a method of eradicating spores at a tissue field includes the following steps of: (i) topically applying a solution containing 0.1% to 1% cetrimide and 50-500 µg/ml toluidene blue or methylene blue; and (ii) illuminating the tissue field with a light having a light wavelength, light dosage and a light dosage rate. The light wavelength may range from about 610 nm to about 680 nm. The light dosage may range from about 10 J/cm$^2$ to about 60 J/cm$^2$. The light dosage rate may range from about 50 mw/cm$^2$ to about 150 mw/cm$^2$. Alternative administrations for the solution containing cetrimide and a photosensitive material may include a local injection, a transdermal patch, or an intravenous injection. Alternative photosensitive materials for use with cetrimide may also be practicable.

Another method of utilizing the present invention to eradicate spores at a tissue field includes the following steps of: (i) topically applying a solution containing 0.1% to 1% Arguard™ and 50-500 µg/ml toluidene blue or methylene blue; and (ii) illuminating the tissue field with a light having a light wavelength, light dosage and a light dosage rate. The light wavelength may range from about 610 nm to about 680 nm. The light dosage may range from about 10 J/cm$^2$ to about 60 J/cm$^2$. The light dosage rate may range from about 50 mw/cm$^2$ to about 150 mw/cm$^2$. Alternative administrations for the solution containing cetrimide and a photosensitive material may include a local injection, a transdermal patch, or an intravenous injection. Alternative photosensitive materials may also be practicable. A similar method may be utilized to eradicate viruses, or virus-infected cellular organisms without eradicating the host cellular organism.

Yet another aspect of the present invention is the use of a photosensitive material and a surfactant as a broad spectrum cellular and acellular organism agent for sterilizing medical equipment, such as endoscopes, from viruses, bacteria, fungus, and spores. A particular application of a sterilization process may include the steps of: (i) providing or disposing a photosensitive material and a surfactant on or upon a tangible apparatus; and (ii) illuminating the apparatus with light at an appropriate wavelength and light dosage to effect a photodynamic reaction for eradicating the cellular and acellular organisms.

One method of practicing the invention may include sterilization of medical equipment, such as an endotracheal tube, via biofilm eradication including the steps of: (i) providing a photosensitive material, such as methylene blue, toluidene blue, etc., and a surfactant, such as SDS, cetrimide, ARGUARD, etc., on surfaces of the endotracheal tube having biofilm contamination; and (ii) illuminating the endotracheal tube with light at an appropriate wavelength and light dosage to effect a photodynamic eradication of cellular and/or acellular organisms in the biofilm. It is envisioned that additional combinations of photosensitive material and surfactant may be utilized to practice this application of biofilm/surface organism eradication.

Yet another aspect of the present invention is the application of a pH specific solution for targeting gram-positive or gram-negative bacteria. By adjusting the pH of the solution with reference to the particular bacteria, an increased kill rate results. The pH of the solution (containing at least a photosensitive material and a surfactant) may be adjusted by buffering agents. Those skilled in the relevant arts will appreciate the various approaches to solution pH determination and modification. For gram-negative bacteria, a preferred pH range of solution is between 5-7.5. For gram-positive bacteria, a preferred pH range of solution is between 7-8.5. In one preferred embodiment of practicing the invention, a combination of SDS and methylene blue and/or toluidene blue was provided in a solution. The solution was selectively adjusted and regulated by buffering agents so that the pH was either between 5-7.5 or 7-8.5, depending on whether gram-negative or gram-positive bacteria were being eradicated by PDT.

Reference may be made to FIG. 5, which illustrates another schedule of results for an investigation of the present invention. The inquiry was made into photoeradication using a solution with a selectively variable pH and including methylene blue. The pH of the solution was varied using known pH testing and adjusting techniques, e.g., buffering agents. The laser used for illumination was a diode laser. Methylene blue concentrations ranged from 7 to 50 µg/ml. Solutions containing various amounts of methylene blue, saline, and bacteria were subjected to various dosages of light and subsequently cultured on a standard plate culture. Light dosages ranged from 20 to 60 J/cm2. Results include a comparison of the colony count of the culture plates with and without light illumination of the solution (L+ and L−). A qualitative colony count relates particular colony counts to an associated score. For instance, a qualitative colony count of 5 would yield a score of '1', while a colony count of 151 would have an associated score of '2'. The numbers in parentheses indicate the actual colony number. The results of the L– column illustrate that in the absence of light, the solution pH and/or methylene blue concentrations have no effect on colony counts (pH of solution and/or methylene blue do not eradicate the bacteria). With application of light to the solutions containing methylene blue, saline, and bacteria, the pH of the solution is associated with the colony counts of the gram negative or gram positive bacteria. As a result, and as illustrated in the L+ column, the effective kill rate of gram negative bacteria, such as Pseudomonas aureus, is associated with solution pH between 5-7.5. Similarly, the effective kill rate of gram positive bacteria, such as *Staphylococcus aureus*, is associated with solution pH between 7.5-8. The results of this investigation demonstrate that the pH of a photosensitizing solution may be manipulated to facilitate selective gram positive or gram negative cell eradication.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

The invention claimed is:

1. A method of photodynamic disruption of cellular organisms comprising:
    applying a surface acting agent in association with a cellular organism, said surface acting agent disorienting a cell membrane so that said cell membrane no longer functions as an effective osmotic barrier, said surface acting agent being a solution selected from the group consisting of SDS with a concentration range of 0.001% to 1.0% and polymyxin B with a concentration range of 3 μg/ml to 500 μg/ml;
    passing a photosensitive material through the disoriented cell membrane and into a cell interior; and
    applying light to photosensitive material within the cell interior to cause a cellular disruption of the cellular organism by a photodynamic reaction of the photosensitive material within the cell interior.

2. The method of cellular organism disruption of claim 1 wherein the step of providing the surface acting agent and the step of providing the photosensitive material occur simultaneously by dispensing a combined solution in proximity to the cellular organism.

3. The method of cellular organism disruption of claim 2 wherein the combined solution is dispensed in proximity to the cellular organism via one or more of the group containing: an injection proximate the cellular organism, an intravenous injection, a subcutaneous injection, and a topical application.

4. The method of cellular organism disruption of claim 1 wherein the cellular organism is gram positive, said method further comprising the step of:
    identifying a surface acting agent from among a group of surface active agents particularly reactive with gram positive cells.

5. The method of claim 4, said method further comprising the steps of:
    providing the surface acting agent in a solution having a pH;
    determining the pH of the solution; and
    adjusting the pH of the solution to within the range of 7-8.5.

6. The method of claim 1, said method further comprising the step of:
    providing the surface acting agent in a solution having a pH;
    determining the pH of the solution; and
    adjusting the pH of the solution to within the range of 5-7.5.

7. The method of cellular organism disruption of claim 1 wherein the photosensitive material is monomeric, dimeric, or polymeric.

8. The method of cellular organism disruption of claim 1 wherein the cellular organism is associated with a sterilization procedure.

9. The method of cellular organism disruption of claim 1 wherein the cellular organism is associated with a biofilm eradication procedure.

10. The method of cellular organism disruption of claim 1 wherein the cellular organism is associated with a treatment of an infection at a tissue site.

11. The method of cellular organism disruption of claim 1 wherein the cellular organism is a microbe, a spore, a fungus, or a cancer cell.

12. The method of cellular organism disruption of claim 1 wherein the surface acting agent is SDS provided in a concentration range of between 0.003% to 0.01%.

13. The method of cellular organism disruption of claim 1 wherein the surface acting agent is polymyxin B provided in a concentration range of between 3 μg/ml to 300 μg/ml.

14. The method of cellular organism disruption of claim 1 wherein the step of providing the surface acting agent precedes the step of providing the photosensitive material by between 1 to 30 minutes.

15. The method of cellular organism disruption of claim 1 wherein the step of applying light results in cellular organism destruction.

16. The method of cellular organism disruption of claim 1 wherein the step of applying light in association with the cellular organism occurs for a period of between 5 seconds to 1 hour and results in cellular organism death.

17. The method of cellular organism disruption of claim 16 wherein the step of applying a light occurs for a period of between 2 to 20 minutes.

18. The method of cellular organism disruption of claim 1 wherein the step of providing the photosensitive material includes providing more than one of a plurality of different photosensitive materials.

19. The method of cellular organism disruption of claim 1 wherein the step of applying a light includes a light wavelength ranging from 450 nm to 700 nm and a light dosage ranging from 10 J/cm2 to 100 J/cm2 and a light dosage rate ranging from 50 mw/cm2 to 250 mw/cm2.

20. The method of cellular organism disruption of claim 1 wherein the cellular organism is from the group containing: eucaryotic cells, prokaryotic cells, obligate intracellular bacteria, bacteria, and cancer cells.

21. The method of cellular disruption of claim 12 wherein the photosensitive material is methylene blue and the cellular organism an eucaryotic cell.

22. A method of photodynamic disruption of acellular organisms comprising:
    providing a surface acting agent in association with an acellular organism, said surface acting agent disorienting a membrane of the acellular organism so that said membrane no longer functions as an effective osmotic barrier, said surface acting agent being a solution selected from the group consisting of SDS with a concentration range of 0.001% to 1.0% and polymyxin B with a concentration range of 3 μg/ml to 500 μg/ml;
    passing a photosensitive material through the disoriented membrane of the acellular organism and into an interior, said photosensitive material being accumulated within the membrane of the acellular organism; and applying light to the photosensitive material within the interior of the acellular organism to cause a disruption of the acellular organism through a photodynamic reaction of the photosensitive material within the acellular organism.

23. The method of acellular organism disruption of claim 22 wherein the step of providing the surface acting agent and the step of disposing the photosensitive material occur simultaneously by dispensing a combined solution in proximity to the acellular organism.

24. The method of acellular organism disruption of claim 22 wherein the combined solution is dispensed in proximity to the acellular organism via one or more of the group containing: an injection proximate the acellular organism, an intravenous injection, a subcutaneous injection, and a topical application.

25. The method of acellular organism disruption of claim 22 wherein the acellular organism is associated with a sterilization procedure.

26. The method of acellular organism disruption of claim 22 wherein the acellular organism is associated with a biofilm eradication procedure.

27. The method of acellular organism disruption of claim 22 wherein the acellular organism is associated with a treatment of an infection at a tissue site.

28. The method of acellular organism disruption of claim 22 wherein the photosensitizing agent is monomeric, dimeric, or polymeric.

29. The method of acellular organism disruption of claim 22 wherein the surface acting agent is SDS provided in a concentration range of between 0.003% to 0.01%.

30. The method of acellular organism disruption of claim 22 wherein the surface acting agent is polymyxin B provided in a concentration range of between 25 µg/ml to 300 µg/ml.

31. The method of acellular organism disruption of claim 22 wherein the step of applying light results in acellular organism destruction.

32. The method of acellular organism disruption of claim 22 wherein the step of applying light occurs for a period of between 5 seconds to 1 hour and results in acellular organism death.

33. The method of acellular organism disruption of claim 32 wherein the step of applying light occurs for a period of between 2 to 20 minutes and results in acellular organism death.

34. The method of acellular organism disruption of claim 22 wherein the step of providing the surface acting agent precedes the step of providing the photosensitive material by between 1 to 30 minutes.

35. The method of acellular organism disruption of claim 22 wherein the step of providing the photosensitive material includes providing more than one of a plurality of different photosensitive materials.

36. The method of acellular organism disruption of claim 22 wherein the step of applying a light includes a light wavelength ranging from 450 nm to 700 nm and a light dosage ranging from 10 J/cm2 to 100 J/cm2 and a light dosage rate ranging from 50 mw/cm2 to 250 mw/cm2.

37. The method of acellular organism disruption of claim 22 wherein the acellular organism is from a group containing: a virus, a spore, and a plasmid.

38. A method of photodynamic disruption of cells comprising the steps of:
identifying an area of cell activity;
providing a concentration including a combination of a chemical agent and a photosensitive material in association with the area of cell activity, said chemical agent being a solution selected from the group consisting of SDS with a concentration range of 0.001% to 1.0% and polymyxin B with a concentration range of 3 µg/ml to 500 µg/ml,
disorienting a cell membrane with the chemical agent so that said membrane no longer functions as an effective osmotic barrier;
passing the photosensitive material through the disoriented cell membrane and into a cell interior; and
exposing the photosensitive material within the cell interior to light having a light wavelength, a light dosage and a light dosage rate to cause photodynamic cellular disruption.

39. The method of photodynamic disruption of cells of claim 38 wherein the step of identifying an area of cell activity includes an examination of a portion of a living body.

40. The method of photodynamic disruption of cells of claim 38 wherein the step of identifying an area of cell activity includes identifying an article of medical apparatus for a sterilization procedure.

41. The method of photodynamic disruption of cells of claim 38 wherein the surfactant is SDS provided in a solution having an SDS concentration range of between 0.003% to 0.01%.

42. The method of photodynamic disruption of cells of claim 38 wherein the concentration is provided in a solution having a pH between 5 to 7.5.

43. The method of photodynamic disruption of cells of claim 38 wherein the concentration is provided in a solution having a pH between 7 to 8.5.

44. The method of photodynamic disruption of cells of claim 38 wherein the step of exposing the area of cell activity to light occurs for a period of between 5 seconds to 1 hour and results in cell death.

45. The method of photodynamic disruption of cells of claim 42 wherein the step of exposing the area of cell activity to light occurs for a period of 2 to 20 minutes.

46. The method of photodynamic disruption of cells of claim 42 wherein the light wavelength ranges from 450 nm to 700 nm, the light dosage ranges from 10 J/cm2 to 100 J/cm2 and the light dosage rate ranges from 50 mw/cm2 to 250 mw/cm2.

47. A treatment protocol for a living body having cancer cells, said protocol comprising the steps of:
selecting a chemical agent to disrupt a cell membrane of a cancer cell, said chemical agent being a solution selected from the group consisting of SDS with a concentration range of 0.001% to 1.0% and polymyxin B with a concentration range of 3 µg/ml to 500 µg/ml;
applying the chemical agent to the cell membrane of the cancer cell, said chemical agent disorienting a cancer cell membrane so that said membrane no longer functions as an effective osmotic barrier;
passing the photosensitive material through the disoriented cancer cell membrane, said photosensitive material accumulating within the cancer cell; and
applying a light to the photosensitive material within the cancer cell, the combination of photosensitive material within the cancer cell and light resulting in disruption of the cancer cell.

48. The treatment protocol according to claim 47 wherein the SDS is provided in a solution having an SDS concentration between 0.003% and 0.01%.

49. The treatment protocol according to claim 47 wherein the steps of administering the chemical agent to the body and administering a photosensitive material to the body are achieved by providing a solution having the chemical agent and the photosensitizing agent and disposing the solution on at least a portion of the body.

50. The treatment protocol of claim 48 wherein the step of disposing the solution on at least a portion of the body includes a solution administration selected from among a group of: topical administration, intravenous administration, subcutaneous administration, and administration proximate to the cancer cell.

51. The treatment protocol of claim 47 wherein the step of applying a light in association to the cancer cell occurs for a period of between 2 to 20 minutes and results in cancer cell death.

52. The treatment protocol according to claim 47 wherein the step of administering the chemical agent to the body includes the step of providing a solution having a plurality of different chemical agents.

53. The treatment protocol according to claim 47 wherein the step of administering the photosensitizing agent to the body includes the step of providing a solution having a plurality of different photosensitive materials.

54. The treatment protocol according to claim 47 wherein the steps of administering the chemical agent and administering the photosensitive material to the body are achieved by providing a solution having a plurality of different chemical agents and a plurality of different photosensitive materials and disposing the solution on at least a portion of the body.

55. The treatment protocol according to claim 47 wherein the step of applying a light includes a light wavelength ranging from 450 nm to 700 nm and a light dosage ranging from 10 J/cm2 to 100 J/cm2 and a light dosage rate ranging from 50 mw/cm2 to 250 mw/cm2.

56. A treatment protocol for a living body infected with a microbial cell, said protocol comprising the steps of:
   selecting a chemical agent, said chemical agent being a solution selected from the group consisting of SDS with a concentration range of 0.001% to 1.0% and polymyxin B with a concentration range of 3 µg/ml to 500 µg/ml;
   administering the chemical agent to the living body to disorient a cell membrane of a microbial cell so that said cell membrane no longer functions as an effective osmotic barrier;
   passing a photosensitive material through the disoriented cell membrane, said photosensitive material accumulating within the microbial cell; and
   applying a light to the photosensitive material within the microbial cell, said light in combination with the photosensitive material within the microbial cell to cause disruption of the microbial cell.

57. The treatment protocol according to claim 56 wherein the chemical agent is administered to the living body between 1 to 30 minutes prior to the step of administering the photosensitive material.

58. The treatment protocol of claim 56 wherein the step of applying the light in association to the microbial cell occurs for a period of between 2 to 20 minutes and results in microbial cell death.

59. The treatment protocol according to claim 56 wherein the steps of administering the chemical agent to the living body and administering a photosensitive material to the body are simultaneously achieved by providing a solution having the chemical agent and the photosensitive material and disposing the solution on at least a portion of the body.

60. The treatment protocol of claim 59 wherein the step of disposing the solution includes a solution administration selected from among a group of: topical administration, intravenous administration, subcutaneous administration, administration proximate the microbial cells, and administration within the microbial cells.

61. The treatment protocol of claim 59 wherein the microbial cells are from a group containing: a cancer cell, an obligate intracellular bacteria, a virus, a fungus, a spore, a eucaryotic cell, and a prokaryotic cell.

62. A kit assembly for potentiation of a photodynamic therapy of a pathogenic organism, said photodynamic therapy utilizing a light source for a photodynamic organism destruction, said kit assembly comprising:
   a surface acting agent, said surface acting agent adapted to disorientate a pathogenic organism membrane so that said membrane no longer functions as an effective osmotic barrier, said surface acting agent being a solution selected from the group consisting of SDS with a concentration range of 0.001% to 1.0% and polymyxin B with a concentration range of 3 µg/ml to 500 µg/ml; and
   a photosensitive material, said photosensitive material passing through the pathogenic organism membrane and into the pathogenic organism cytoplasm, wherein said photosensitive material is reactive with the light source to result in the photodynamic organism destruction of the pathogenic organism.

63. The kit according to claim 62 wherein the surface acting agent and the photosensitive material are provided in combined solution.

64. The kit according to claim 62 wherein the surface acting agent and the photosensitive material are provided in a combined solution having a plurality of different surface acting agents and a plurality of different photosensitive materials.

65. The kit according to claim 62 wherein the surface acting agent is applied to a cell site of a medical device prior to an application of the photosensitive material.

66. The kit according to claim 65 wherein the surface acting agent is applied to the cell site between 1 to 30 minutes prior to application of the photosensitive material.

67. The kit according to claim 63 wherein the combined solution has a selectively variable pH.

68. The kit according to claim 67 wherein the combined solution pH is between 5 to 7.5 and the combined solution is for eradication gram negative bacteria.

69. The kit according to claim 67 wherein the combined solution pH is between 7 to 8.5 and the combined solution is for eradication of gram positive bacteria.

70. The kit according to claim 62 further comprising a plurality of different surface acting agents.

71. The kit according to claim 62 further comprising a plurality of different photosensitive materials.

72. The kit according to claim 62 further comprising a light source for initiating a photodynamic reaction.

73. The kit according to claim 71 wherein the light source is a fiber optic light guide for coupling to a remote light source.

* * * * *